US009505693B2

(12) United States Patent
Nieuwhof et al.

(10) Patent No.: US 9,505,693 B2
(45) Date of Patent: Nov. 29, 2016

(54) PROCESS FOR THE HYDRODECHLORINATION OF A LIQUID FEED COMPRISING DICHLOROACETIC ACID

(71) Applicants: Melle Rinze Nieuwhof, Dieren (NL); Cornelis Kooijman, Deventer (NL); Hendrik Jan Vos, Apeldoorn (NL); Lars Magnus Tollin, Skoghall (SE); Jacobus Van Den Berg, Voorthuizen (NL); Henricus Johannes Marinus Petrus Van Hal, Barneveld (NL)

(72) Inventors: Melle Rinze Nieuwhof, Dieren (NL); Cornelis Kooijman, Deventer (NL); Hendrik Jan Vos, Apeldoorn (NL); Lars Magnus Tollin, Skoghall (SE); Jacobus Van Den Berg, Voorthuizen (NL); Henricus Johannes Marinus Petrus Van Hal, Barneveld (NL)

(73) Assignee: Akzo Nobel Chemicals International B.V., Velperweg (NL)

( * ) Notice: Subject to any disclaimer, the term of this patent is extended or adjusted under 35 U.S.C. 154(b) by 0 days.

(21) Appl. No.: 14/351,331

(22) PCT Filed: Oct. 17, 2012

(86) PCT No.: PCT/EP2012/070524
§ 371 (c)(1),
(2) Date: Apr. 11, 2014

(87) PCT Pub. No.: WO2013/057126
PCT Pub. Date: Apr. 25, 2013

(65) Prior Publication Data
US 2014/0357892 A1 Dec. 4, 2014

(30) Foreign Application Priority Data
Oct. 20, 2011 (EP) .................................. 11185953

(51) Int. Cl.
C07C 51/347 (2006.01)
C07C 51/487 (2006.01)

(52) U.S. Cl.
CPC .......... C07C 51/347 (2013.01); C07C 51/487 (2013.01)

(58) Field of Classification Search
None
See application file for complete search history.

(56) References Cited

U.S. PATENT DOCUMENTS

| 2,539,238 | A | 1/1951 | Eaker |
| 2,671,803 | A | 3/1952 | Sennewald et al. |
| 2,863,917 | A | 12/1958 | Rucker et al. |
| 3,754,029 | A | 8/1973 | Freyer et al. |
| 4,051,019 | A | 9/1977 | Johnson |
| 4,159,785 | A | 7/1979 | Berry, Jr. |
| 4,636,353 | A | 1/1987 | Seon et al. |
| 5,191,118 | A | 3/1993 | Correia et al. |
| 5,356,850 | A | 10/1994 | Correia et al. |
| 5,414,116 | A | 5/1995 | Correia |
| 5,449,501 | A | 9/1995 | Luebke et al. |
| 5,466,650 | A | 11/1995 | Correia |
| 5,758,699 | A | 6/1998 | Haquet et al. |

FOREIGN PATENT DOCUMENTS

| CN | 101528657 | 9/2012 |
| DE | 1 072 980 | 1/1960 |
| DE | 1 816 931 | 7/1970 |
| DE | 43 27 872 | 3/1994 |
| EP | 0 453 690 | 10/1991 |
| EP | 0 557 169 | 8/1993 |
| EP | 0 727 250 | 8/1996 |
| EP | 0 728 730 | 8/1996 |
| EP | 0 769 462 | 4/1997 |
| EP | 1451136 | 1/2004 |
| GB | 1 249 718 | 10/1971 |
| GB | 1 411 214 | 10/1975 |
| JP | 2003-144921 | 5/2003 |
| JP | 2008-183558 | 8/2008 |
| NL | 109769 | 10/1964 |
| RU | 2301331 | 6/2007 |
| RU | 2 318 796 | 9/2009 |
| RU | 2391331 | 2/2010 |
| WO | 2008/025758 | 3/2008 |
| WO | 2008/109671 | 9/2008 |

OTHER PUBLICATIONS

Gaetan, Mary et al., "Trickle-Bed Laboratory Reactors for Kinetic Studies", International Journal of Chemical Reactor Engineering, 2009, vol. 7, pp. 1-68.

(Continued)

Primary Examiner — Yong Chu
Assistant Examiner — Ana Z Muresan
(74) Attorney, Agent, or Firm — McDonnell Boehnen Hulbert & Berghoff LLP

(57) ABSTRACT

The process of the present invention pertains to a process wherein a liquid feed comprising monochloroacetic acid, dichloroacetic acid, and optionally acetic acid and/or trichloroacetic acid is subjected to a catalytic hydrodechlorination step by contacting it with a source of hydrogen in the presence of a solid heterogeneous hydrogenation catalyst situated in a fixed catalyst bed, wherein the liquid feed is fed to the top of avertical tubular reactor at a superficial mass velocity of between and 10 kg/s per square meter of the horizontal cross-section of the vertical tubular reactor and a rate of between 250 and 3,000 kg/hr per m of said catalyst bed, wherein the source of hydrogen is fed to the top or bottom of the vertical tubular reactor at a rate of between 0.025 to 0.25 Nm/s per square meter of the horizontal cross-section of the vertical tubular reactor, so as to obtain an average axial pressure gradient of at least 2 kPa per meter of said catalyst bed, and wherein the temperature in the top of the vertical tubular reactor is between 100 and 200° C., and wherein the pressure in the top of the vertical tubular reactor is between 0.2 and 1.0 MPa.

20 Claims, No Drawings

(56) References Cited

OTHER PUBLICATIONS

Shah, Y.T., Gas liquid solid reactor design, McGraw-Hill, Inc. 1979, p. 93.
Westerterp & Wammes (K Roel Westerterp and Wino J.S. Wammes), "Three-phase trickle-bed reactors", Ullmann's Encyclopedia of Industrial Chemistry, Wiley-VCH Verlag GmbH & Co. KgAA, weinheim, 2013 version, pp. 1-34 (corresponds to a newer version of 2005 cited reference).
International Search Report for International Application No. PCT/EP2012/070524, mailed on Nov. 11, 2012.
International Preliminary Report on Patentability for International Application No. PCT/EP2012/070524, issued on Apr. 22, 2014.
Hofmann, Hans, "Hydrodynamics and Hydrodynamic Models of Fixed Bed Reactors," Chapter 8, in Agostino Gianetto and Peter L. Silveston (eds.), Multiphase Chemical Reactors—Theory, Design, Scale-up, Hemispere Publishing Co., 1986, p. 256-257.
European Search Report for EP Application No. 11185953.4, mailed on Apr. 5, 2012.
Saroha, Anil K. and Nigam, K.D.P., "Trickle-bed Reactros," Reviews in Chemical Engineering, 12, 3-4, 207-347, 1996.
Griffioen, Gert and Wijbrands, Michel, "Caring for Catalysts," Hydrocarbon Engineering, Jun. 2010.
DIN EN ISO 6271-1, Clear Liquids, Estimation of colour by the platinum—cobalt scale, Part 1: Visual method, ISO 6271-1:2004, Mar. 2005.
International Search Report for International Application No. PCT/EP2012/070523, mailed on Nov. 20, 2012.
International Preliminary Report on Patentability for International Application No. PCT/EP2012/070523, issued on Apr. 22, 2014.
DIN EN ISO 6271-2, Clear Liquids, Estimation of colour by the platinum—cobalt scale, Part 2: Spectrophotometric method ISO 6271-2:2004, Mar. 2005.
European Search Report for EP Application No. 11185948.4, mailed on Apr. 5, 2012.
Third Party Observations received in EP Application No. 12 775 481.0, dated on Jan. 26, 2016.
Third Party Observations received in corresponding EP Application No. 12 778 693.7, dated Jan. 26, 2016.
Sie, S.T., et al., Process Development and Scale Up: III. Scale-up and scale-down of trickle bed processes, Reviews in Chemical Engineering, 1998, vol. 14, No. 3, pp. 203-248.
Bhaskar, M., et al., Three-Phase Reactor Model to Simulate the Performance of Pilot-Plant and Industrial Trickle-Bed Reactors Sustaining Hydrotreating Reactions, Ind. Eng. Chem. Res., 2004, vol. 43, No. 21, pp. 6654-6669.

PROCESS FOR THE HYDRODECHLORINATION OF A LIQUID FEED COMPRISING DICHLOROACETIC ACID

REFERENCE TO RELATED APPLICATIONS

This application is the U.S. National Phase of PCT/EP2012/070524, filed on Oct. 17, 2012, and claims the benefit of EP Application No. 11185953.4, filed on Oct. 20, 2011.

The present invention relates to a process for the hydrodechlorination of a liquid feed comprising dichloroacetic acid (DCA).

The predominant industrial route for the production of monochloroacetic acid is by reacting acetic acid with chlorine. Such a process is commonly known and generally makes use of a reactor in which a mixture of liquid acetic acid (HAc) is reacted with chlorine under anhydrous conditions, using acetyl chloride as the catalyst. Acetyl chloride is preferably formed in-situ by the addition of e.g. acetic anhydride. In the chlorination reactor, monochloroacetic acid (MCA) and gaseous HCl are formed together with by-products of which dichloroacetic acid (DCA) and trichloroacetic acid (TCA) are examples.

After the MCA-containing reaction product mixture has passed the reactor(s) and the catalyst recovery section, DCA is present in a significant amount, typically about 3-10%. To reduce the amount of DCA in the MCA, the MCA/DCA-containing product mixture is subsequently subjected to a purification process. The purification process can either be a physical separation, such as crystallization or distillation, or a chemical conversion, such as a reduction where DCA is reduced with hydrogen in the presence of a hydrogenation catalyst, e.g. a metal-based catalyst.

As the boiling points of monochloroacetic acid and dichloroacetic acid are very close (189° and 194° C., respectively), removal of DCA from MCA by distillation is expensive and uneconomical.

With crystallization, the concentration of dichloroacetic acid in a crude monochloroacetic acid feed can only be reduced by a factor of approximately 4, i.e., for example, from 3 to 0.7-0.8% by weight, with a one-stage recrystallization. Hence, for the production of pure monochloroacetic acid, the space and time requirements are considerable. Furthermore, after several crystallizations, a mother liquor remains comprising a mixture of monochloroacetic acid and dichloroacetic acid. Although this mother liquor still comprises at least 30% by weight of monochloroacetic acid, depending on the cooling conditions, it cannot be converted into a saleable product by further crystallization and has to be regarded as waste.

It is known that the concentration of dichloroacetic acid in crude monochloroacetic acid can be reduced considerably by a catalytic hydrodechlorination (for example in accordance with U.S. Pat. No. 5,191,118 and U.S. Pat. No. 5,356,850).

This reaction can be carried out in the vapour phase (for example in accordance with NL 109,769 and DE 1,072,980). However, this vapour phase reaction requires the evaporation of the feed to the hydrodechlorination reactor, which is unattractive with respect to energy consumption and investment costs for required heat transfer equipment.

Alternatively, the hydrodechlorination is carried out in slurry reactors in which the catalyst is finely dispersed in the liquid phase (for example in accordance with U.S. Pat. No. 2,863,917, DE 1,816,931 and WO 2008/025758). The troublesome separation of the finely dispersed catalyst from the liquid phase is a significant disadvantage of these reactor types and the high degree of backmixing, in case of continuous operation of these reactors, will require multiple reactors in series to achieve high conversions. The latter will lead to high investment costs.

Another possibility is to feed the liquid crude monochloroacetic acid to the top of a vertical tubular reactor in which it trickles downwards over a heterogeneous catalyst that is accommodated in a fixed bed, while hydrogen is fed to the top or bottom of the vertical tubular reactor (for example in accordance with U.S. Pat. No. 3,754,029). These reactors are commonly known as trickle-bed reactors). However, from a hydrodynamic point of view this way of operation (with the gas in countercurrent flow) is disadvantageous, as it limits the capacity of the reactor column by flooding.

It is therefore preferred to feed the liquid crude monochloroacetic acid to the top of a vertical tubular reactor, in which it trickles down over a heterogeneous catalyst that is accomodated in a fixed bed, with cocurrent downflow of the source of hydrogen (as also mentioned in U.S. Pat. No. 3,754,029, RU 2,318,796, or RU 2,391,331). This way of operation prevents the excessive use of energy for the evaporation of the liquid feed to the reactor column, circumvents the troublesome separation of finely dispersed catalyst in slurry reactors, and allows for a broader operating window in comparison with trickle-bed reactors operated with countercurrent flow of the source of hydrogen.

The design and scale-up of these trickle-bed reactors (also denoted throughout this specification as vertical tubular reactors) is very complex due to complicated hydrodynamics, as argued by e.g. Shah (Y. T. Shah, *Gas-liquid-solid reactor design*, McGraw-Hill Inc., 1979, p. 93), Westerterp & Wammes (K. Roel Westerterp, Wino J. A. Wammes: "Three-Phase Trickle-Bed Reactors" in *Ullmann's Encyclopedia of Industrial Chemistry*, Wiley-VCH Verlag GmbH & Co. KGaA, weinheim, 2005, and Hofmann (Hans Hofmann, "Hydrodynamics and hydrodynamic models of fixed bed reactors" in Agostini Gianetto and Peter L. Silveston (eds.), *Multiphase chemical reactors—theory, design, scale-up*, Hemishere Publishing Co., 1986). Moreover, it is impossible to operate a laboratory vertical tubular reactor and an industrial vertical tubular reactor simultaneously at the same liquid hourly space velocity (i.e. the amount of liquid fed to the reactor per hour and per unit volume of catalyst) and superficial mass velocity (i.e. the amount of liquid fed to the reactor per square meter cross-section), due to the large difference between the geometry of such units (see Mary et al., "Trickle-Bed Laboratory Reactors for Kinetic Studies," *International Journal of Chemical Reactor Engineering*, Vol. 7: R2, 2009).

It is an object of the present invention to provide an industrial scale process for the purification of monochloroacetic acid by the catalytic hydrodechlorination of dichloracetic acid (and optionally trichloroacetic acid) in a vertical tubular reactor, wherein a higher mass transfer rate is achieved combined with a residence time distribution close to that of plug flow and wherein a higher conversion is achieved.

By an "industrial scale process" is meant that the catalytic hydrodechlorination step is carried out in an industrial scale sized vertical tubular reactor, hereinafter meaning a vertical tubular reactor having a diameter equal to or greater than 0.4 m.

Another object of the present invention is to provide an industrial scale process for the purification of monochloroacetic acid by the catalytic hydrodechlorination of dichloracetic acid (and optionally trichloroacetic acid) in a vertical tubular reactor while minimizing the required catalyst inventory.

It has surprisingly been found that these objectives are met when, for a vertical tubular reactor having a certain diameter, the superficial mass velocity of the liquid and the superficial gas velocity are within a certain range so that a relatively high average axial pressure gradient is obtained. More specifically, the present invention relates to a process wherein a liquid feed comprising monochloroacetic acid, dichloroacetic acid, and optionally acetic acid and/or trichloroacetic acid is subjected to a catalytic hydrodechlorination step by contacting it with a source of hydrogen to convert the dichloroacetic acid into monochloroacetic acid in the presence of a solid heterogeneous hydrogenation catalyst comprising one or more metals of Group VIII of the Periodic Table of the Elements deposited on a carrier, characterized in that said catalytic hydrodechlorination step is carried out in a vertical tubular reactor with a diameter exceeding 0.4 m, with the solid heterogeneous hydrogenation catalyst being situated in a fixed catalyst bed, wherein the liquid feed is fed to the top of said vertical tubular reactor at a superficial mass velocity of between 1 and 10 kg/s per square meter of the horizontal cross-section of the vertical tubular reactor and a rate of between 250 and 3000 kg/hr per m$^3$ of said catalyst bed, wherein the source of hydrogen is fed to the top or bottom of the vertical tubular reactor at a superficial gas velocity of between 0.025 to 0.25 Nm$^3$/s per square meter of the horizontal cross-section of the vertical tubular reactor, so as to obtain an average axial pressure gradient of at least 2 kPa per meter of said catalyst bed, and wherein the temperature in the top of the vertical tubular reactor is between 100 and 200° C., and wherein the pressure in the top of the vertical tubular reactor is between 0.2 and 1.0 MPa.

In a preferred embodiment, the liquid feed which is fed to the top of the vertical tubular reactor comprises at least 5.5% by weight of acetic acid. The acetic acid will partly evaporate in the trickle-bed reactor and thus increases the pressure drop over the reactor, resulting in a higher mass transfer coefficient.

The heterogeneous hydrogenation catalyst according to the present invention preferably comprises between 0.1 and 3% by weight, more preferably between 0.5 and 2% by weight, based on the total weight of the heterogeneous catalyst, of one or more metals of Group VIII of the Periodic Table of the Elements. Preferably, the heterogeneous catalyst comprises ruthenium, rhodium, palladium and/or platinum. More preferably, it comprises palladium, platinum, or a combination thereof. Most preferably, it comprises palladium (Pd) and either sulfur or a sulfur compound. For example, the catalyst described in EP 0557169 or the catalysts as described in EP 0453690 are suitable for use in the present process.

The carrier on which the one or more metals of Group VIII of the Periodic Table of the Elements have been deposited is preferably selected from the group consisting of activated carbon, silica, alumina, zirconium oxide, and titanium oxide. Activated carbon is most preferred. The carrier may comprise sulfur or sulfur-containing components (either organic or inorganic in nature).

In a preferred embodiment, the heterogeneous catalyst which is used in step (b) of the process according to the present invention is palladium on an activated carbon carrier, while sulfur or sulfur-containing components such as CS$_2$ may be added to the feed.

In one embodiment, the one or more metals of the heterogenous hydrogenation catalyst have been deposited on particles prepared from activated carbon, silica, or alumina, said particles being in the form of irregularly shaped granules, spheres, rings, trilobes, quadrulobes, or extrudates. More preferably, said particles are in the form of extrudates, trilobes, or quadrulobes, having a diameter of between 0.5 and 5 mm, preferably 0.8 to 3 mm, and a length of between 1 to 10 mm.

The catalyst is situated in a fixed catalyst bed. This fixed bed can consist of one single bed, or may be subdivided into multiple sub-beds that are together called "the fixed catalyst bed". The catalyst bed or each sub-bed are supported by a support grid. Furthermore, a liquid distributor may be mounted above the surface of the entire catalyst bed and/or above the surface of one or more sub-beds to provide for a good liquid distribution over the diameter of said catalyst bed.

Suitable construction materials for these column internals (i.e. the support grid and the liquid distributor) include glass lined steel; tantalum and tantalum alloys, including tantalum claddings or coatings on steel or stainless steel; platinum and platinum alloys, including platinum claddings or coatings on steel or stainless steel; zirconium and zirconium alloys, including zirconium claddings or coatings on steel or stainless steel; graphite or impregnated graphite; ceramics—such as e.g. silicon carbide (SiC), zirconia (ZrO$_2$), alumina (Al$_2$O$_3$), glas, or quartz; acid resistant bricks; polytetrafluorethylene (PTFE); fluoropolymer—e.g. PTFE, perfluoralkoxy polymers (PFA), fluorinated ethylene-propylene (FEP) or polyethylenechlorotrifluoroethylene (ECTFE)—linings or coatings on steel, stainless steel, or fiber-reinforced plastics; nickel-chromium alloys; nickel-chromium-molybdenum alloys; nickel-copper alloys; silver, including silver claddings or silver coatings on steel or stainless steel; niobium and niobium alloys; and polyether ether ketone and PEEK-coated steel.

Preferred construction materials for the internals are glass lined steel; tantalum and tantalum alloys, including tantalum claddings or coatings on steel or stainless steel; platinum and platinum alloys, including platinum claddings or coatings on steel or stainless steel; zirconium and zirconium alloys, including zirconium claddings or coatings on steel or stainless steel; graphite or impregnated graphite; ceramics—such as silicon carbide (SiC), zirconia (ZrO$_2$), alumina (Al$_2$O$_3$), glass, or quartz; acid resistant bricks; polytetrafluorethylene (PTFE); fluoropolymer—e.g. PTFE, perfuloralkoxy polymers (PFA), fluorinated ethylene-propylene (FEP) or polyethylenechlorotrifluoroethylene (ECTFE)—linings or coatings on steel, stainless steel, or fiber-reinforced plastics.

More preferred construction material of the internals are glass lined steel; graphite or impregnated graphite; tantalum and tantalum alloys, including tantalum claddings or coatings on steel or stainless steel; and zirconium and zirconium alloys, including zirconium claddings or coatings on steel or stainless steel.

Most preferably, the construction material for the internals is graphite or impregnated graphite.

The source of hydrogen that is fed to the purification process according to the present invention is a source of hydrogen gas, which can either be substantially pure hydrogen gas or a gas comprising hydrogen gas and up to 50 mole % of nitrogen, hydrogen chloride, or a mixture thereof.

The hydrodechlorination step is carried out using a vertical tubular reactor containing the solid heterogeneous hydrogenation catalyst as described above in a fixed bed (also sometimes denoted as a stationary bed of catalyst particles).

Suitable reactor construction materials include glass lined steel; tantalum and tantalum alloys, including tantalum claddings or coatings on steel or stainless steel; platinum and platinum alloys, including platinum claddings or coatings on steel or stainless steel; zirconium and zirconium alloys, including zirconium claddings or coatings on steel or stainless steel; graphite or impregnated graphite; ceramics—e.g. silicon carbide (SiC), zirconia ($ZrO_2$), alumina ($Al_2O_3$), glas and quartz; acid resistant bricks, polytetrafluorethylene (PTFE); fluoropolymer—e.g. PTFE, perfuloralkoxy polymers (PFA), fluorinated ethylene-propylene (FEP) or polyethylenechlorotrifluoroethylene (ECTFE)—linings or coatings on steel, stainless steel, or fiber-reinforced plastics; nickel-chromium alloys; nickel-chromium-molybdenum alloys; nickel-copper alloys; silver, including silver claddings or silver coatings on steel or stainless steel; niobium and niobium alloys; and polyether ether ketone or PEEK coated steel.

Preferred construction materials are glass lined steel; tantalum and tantalum alloys, including tantalum claddings or coatings on steel or stainless steel; platinum and platinum alloys, including platinum claddings or coatings on steel or stainless steel; zirconium and zirconium alloys, including zirconium claddings or coatings on steel or stainless steel; graphite or impregnated graphite; ceramics—such as silicon carbide (SiC), zirconia ($ZrO_2$), alumina ($Al_2O_3$), glass and quartz; acid resistant bricks; polytetrafluorethylene (PTFE); fludropolymer—e.g. PTFE, perfuloralkoxy polymers (PFA), fluorinated ethylene-propylene (FEP), or polyethylenechlorotrifluoroethylene (ECTFE)—linings or coatings on steel, stainless steel, or and fiber-reinforced plastics.

More preferably, the construction material is selected from the group consisting of glass lined steel; tantalum and tantalum alloys, including tantalum claddings or coatings on steel or stainless steel; and zirconium and zirconium alloys, including zirconium claddings or coatings on steel or stainless steel.

The most preferred construction material is glass lined steel.

The liquid feed comprising monochloroactic acid, dichloroacetic acid, and optionally acetic acid and/or trichloroacetic acid is fed to the top of the vertical tubular reactor. The hydrogen gas or the mixture of hydrogen gas and up to 50 mole % of an inert gas is preferably fed to the top of the vertical tubular reactor (resulting in a co-current downflow with the liquid feed). The hydrogen gas or mixture of hydrogen gas and up to 50 mol % of an inert gas can also be fed from the bottom of the vertical tubular reactor (i.e. in countercurrent with the liquid feed); however, as the operating window is smaller (i.e. the capacity of the reactor is limited by flooding), the co-current downflow embodiment is preferred.

As mentioned above, the liquid feed is fed to the top of said vertical tubular reactor at a superficial mass velocity of between 1 and 10 kg/s per square meter of the horizontal cross-section of said reactor (the term superficial mass velocity (kg/m$^2$/s) refers to the mass flow divided by the horizontal cross-sectional area of said reactor). Preferably, it is fed to the top of said vertical tubular reactor at a superficial mass velocity of at least 2 kg/s per square meter of the horizontal cross-section of said reactor, more preferably at least 2.5 kg/s per square meter of the horizontal cross-section of said reactor, and most preferably at least 3 kg/s per square meter of the horizontal cross-section of said reactor. Preferably, the liquid feed is fed to the top of said vertical tubular reactor at a superficial mass velocity of at most 8 kg/s per square meter of the horizontal cross-section of said reactor, more preferably at a superficial mass velocity of at most 7 kg/s per square meter of the horizontal cross-section of said reactor, and most preferably at a superficial mass velocity of at most 6 kg/s per square meter of the horizontal cross-section of said reactor.

The source of hydrogen is fed to the top of the vertical tubular reactor at a superficial gas velocity of between 0.025 to 0.25 Nm$^3$/s per square meter of the horizontal cross-section of the vertical tubular reactor (the term superficial gas velocity (m/s) refers to the gas velocity based on the horizontal cross-section of said vertical tubular reactor). Preferably, the source of hydrogen is fed to the top or bottom of the vertical tubular reactor at a superficial gas velocity of at least 0.03 Nm$^3$/s per square meter of the horizontal cross-section of the vertical tubular reactor, more preferably at a superficial gas velocity of at least 0.035 Nm$^3$/s per square meter of the horizontal cross-section of the vertical tubular reactor, and most preferably at a superficial gas velocity of at least 0.04 Nm$^3$/s per square meter of the horizontal cross-section of the vertical tubular reactor. Preferably, it is fed at a superficial gas velocity of at most 0.25 Nm$^3$/s per square meter of the horizontal cross-section of the vertical tubular reactor, more preferably of at most 0.20 Nm$^3$/s per square meter of the horizontal cross-section of the vertical tubular reactor, and most preferably of at most 0.15 Nm$^3$/s per square meter of the horizontal cross-section of the vertical tubular reactor.

The temperature in the top of the reactor is preferably kept between 100 and 200° C., and more preferably between 145 and 175° C. The pressure in the top of the vertical tubular reactor is preferably kept between 0.2 and 1.0 MPa, preferably between 0.3 and 0.6 MPa.

In order to minimize the risk of liquid maldistribution in the trickle-bed reactor (see e.g. Saroha & Nigam, "Trickle-bed reactors," *Reviews in Chemical Engineering*, 12, 3-4, 207-347, 1996), the fixed bed in which the heterogeneous hydrogenation catalyst is situated has preferably been prepared by loading the vertical tubular reactor with the heterogeneous hydrogenation catalyst using a dense loading technique. Maldistribution in catalyst beds is known to significantly decrease the reactor's performance and run-time. The dense loading technique is a conventional loading technique whereby the vertical tubular reactor is loaded with particles of catalyst simultaneously over the entire cross-section of said reactor. The result is that a catalyst bed is obtained which is uniformly loaded and wherein the density is increased when compared to other reactor loading techniques. When compared to sock loading, a well known loading technique, the density of the catalyst bed has increased by on average at least 10%, as can be found in Gert Griffioen and Michel Wijbrands, "Caring for Catalysts," *Hydrocarbon Engineering, June* 2010 by. The fixed bed with densely loaded catalyst according to the present invention can for instance be prepared using the well-known Densicat® or the Catapac™ technique. Suitable dense loading methods and equipment are described in EP 769,462, U.S. Pat. No. 4,051,019, U.S. Pat. No. 4,159,785, EP 0727250, WO 2008/109671, and U.S. Pat. No. 5,449,501.

The liquid feed to be subjected to the process according to the present invention preferably comprises
  (i) between 60 and 99.5% by weight of monochloroacetic acid,
  (ii) between 0.05 and 20% by weight, preferably between 1 and 12% by weight, of dichloroacetic acid,
  (iii) between 0 and 30% by weight of acetic acid, (iv) between 0.1 and 5% by weight of water, preferably between 0.1 and 1% by weight of water, most preferably between 0.1 and 0.5% by weight of water, and (v) between 0 and 5% by weight of other components, up to a total of 100%, based on the total weight of the liquid feed.

Other components may include a minor amount of acid anhydrides, trichloroacetic acid, bromoacetic acid, and alpha-chloropropionic acid. It is noted that due to the presence of the water, acid chlorides cannot be present in said liquid feed.

The liquid feed to be subjected to the process according to the present invention preferably comprises at least 5.5% by weight of acetic acid, more preferably at least 6% by weight of acetic acid, and most preferably at least 8% by weight of acetic acid, based on the total weight of the liquid feed. Preferably, no more than 20% of acetic acid is present in the liquid feed, more preferably no more than 12% by weight of acetic acid is present in the liquid feed, based on the total weight of the liquid feed.

The process according to the present invention is further illustrated by the following non-limiting examples.

COMPARATIVE EXAMPLE 1

A liquid feed of 1,620 kg/h comprising 88.1% monochloroacetic acid, 4.1% dichloroacetic acid, 5.4% acetic acid, 1.9% HCl, and 0.5% water was mixed with 3.86 kg/h hydrogen. The resulting gas-liquid mixture was heated to 171° C. and fed to the top of a vertical column with a diameter of 0.8 m and a length of 16 m. The vertical column was filled with a catalyst comprising 1% of Pd on an activated carbon support (catalyst particles comparable to those described in Example 1 of EP 0557169). The catalyst particles were loaded into the reactor by first filling the reactor with water and (slowly) adding the catalyst. Where necessary, water was allowed to drain via the bottom of the reactor to prevent the reactor from overflowing during its filling with catalyst. The reactor is completely drained after all the required catalyst has been added. The catalyst particles were in the form of extrudates having a diameter of 1.5 mm and an average length over diameter ratio of 1.84. The pressure in the top of the column was maintained at 0.32 MPa. The pressure drop over the vertical column was 4 kPa. The gas flow from the bottom of the reactor was passed over a condenser and the condensed vapours were mixed with the liquid leaving the bottom of the reactor, resulting in a crude mixture comprising 0.19% dichloroacetic acid. The final monochloroacetic acid product comprised 0.20% dichloroacetic acid, after distilling off the light and heavy ends.

EXAMPLE 2

A liquid feed of 1,620 kg/h comprising 88.1% monochloroacetic acid, 4.1% dichloroacetic acid, 5.4% acetic acid, 1.9% HCl, and 0.5% water was mixed with 3.86 kg/h hydrogen. The resulting gas-liquid mixture was heated to 171° C. and fed to the top of a vertical column with a diameter of 0.6 m and a length of 16 m, reducing the catalyst inventory from 8 m$^3$ to 4.5 m$^3$. The vertical column was filled with a catalyst comprising 1% of Pd on an activated carbon support (catalyst particles comparable to those described in Example 1 of EP 0557169). The catalyst particles were loaded into the reactor by first filling the reactor with water and (slowly) adding the catalyst. Where necessary, water was allowed to drain via the bottom of the reactor to prevent the reactor from overflowing during its filling with catalyst. The reactor is completely drained after all the required catalyst has been added. The catalyst particles were in the form of extrudates having a diameter of 1.5 mm and an average length over diameter ratio of 1.84. The pressure in the top of the column was maintained at 0.32 MPa. The pressure drop over the vertical column was 27 kPa. The gas flow from the bottom of the reactor was passed over a condenser and the condensed vapours were mixed with the liquid leaving the bottom of the reactor, resulting in a crude mixture comprising 0.11% dichloroacetic acid. The final monochloroacetic acid product, after distilling off the light and heavy ends, comprised 0.11% dichloroacetic acid.

The results as shown in Comparative Example 1 and Example 2 clearly show that with less catalyst (in a column having a smaller diameter), a purer product is obtained.

EXAMPLE 3

A liquid feed of 1,620 kg/h comprising 88.1% monochloroacetic acid, 4.1% dichloroacetic acid, 8.5% acetic acid, 1.9% HCl, and 0.5% water was mixed with 3.86 kg/h hydrogen. The resulting gas-liquid mixture was heated to 171° C. and fed to the top of a vertical column with a diameter of 0.6 m and a length of 16 m. The vertical column was filled with a catalyst comprising 1% of Pd on an activated carbon support (catalyst particles comparable to those described in Example 1 of EP 0557169). The catalyst particles were loaded into the reactor by first filling the reactor with water and (slowly) adding the catalyst. Where necessary, water was allowed to drain via the bottom of the reactor to prevent the reactor from overflowing during its filling with catalyst. The reactor is completely drained after all the required catalyst has been added. The catalyst particles were in the form of extrudates having a diameter of 1.5 mm and an average length over diameter ratio of 1.84. The pressure in the top of the column was maintained at 0.32 MPa. The pressure drop over the vertical column was 32 kPa. The gas flow from the bottom of the reactor was passed over a condenser and the condensed vapours were mixed with the liquid leaving the bottom of the reactor, resulting in a crude mixture comprising 0.083% dichloroacetic acid. The final monochloroacetic acid product, after distilling off the light and heavy ends, comprised 0.093% dichloroacetic acid.

This Example shows that with an increased acetic acid content in the feed and as a result thereof a higher average axial pressure gradient, an even purer product is obtained.

EXAMPLE 4

A liquid feed of 1,620 kg/h comprising 88.1% monochloroacetic acid, 4.1% dichloroacetic acid, 8.5% acetic acid, 1.9% HCl, and 0.5% water was mixed with 3.86 kg/h hydrogen. The resulting gas-liquid mixture was heated to 171° C. and fed to the top of a vertical column with a diameter of 0.6 m and a length of 16 m. The vertical column was filled with a catalyst comprising 1% of Pd on an activated carbon support (catalyst particles comparable to those described in Example 1 of EP 0557169). The reactor was filled with catalyst by means of the Densicat® dense loading technique. Other dense loading techniques, including e.g. the Catapac™ dense loading technique, are also suitable. The catalyst particles were in the form of extrudates having a diameter of 1.5 mm and an average length over diameter ratio of 1.84. The pressure in the top of the column was maintained at 0.32 MPa. The pressure drop over the vertical column was 137 kPa. The gas flow from the bottom of the reactor was passed over a condenser and the condensed vapours were mixed with the liquid leaving the bottom of the reactor, resulting in a crude mixture comprising 0.008% dichloroacetic acid. The final monochloroacetic acid product, after distilling off the light and heavy ends, comprised 0.009% dichloroacetic acid.

The difference between Example 3 and Example 4 is that in Example 4, the catalyst was loaded using a dense loading technique (resulting in an even higher average axial pressure gradient). This results in an even purer product.

EXAMPLE 5

A liquid feed of 4,043 kg/h comprising 88.1% monochloroacetic acid, 4.1% dichloroacetic acid, 5.4% acetic acid, 1.9% HCl, and 0.5% water was mixed with 8.91 kg/h hydrogen. The resulting gas-liquid mixture was heated to 171° C. and fed to the top of a vertical column with a diameter of 0.8 m and a length of 16 m. The vertical column was filled with a catalyst comprising 1% of Pd on an activated carbon support (catalyst particles comparable to those described in Example 1 of EP 0557169). The catalyst particles were loaded into the reactor by first filling the reactor with water and (slowly) adding the catalyst. Where necessary, water was allowed to drain via the bottom of the reactor to prevent the reactor from overflowing during its filling with catalyst. The reactor is completely drained after all the required catalyst has been added. The catalyst particles were in the form of extrudates having a diameter of 1.5 mm and an average length over diameter ratio of 1.84. The pressure in the top of the column was maintained at 0.4 MPa. The pressure drop over the vertical column was 31 kPa. The gas flow from the bottom of the reactor was passed over a condenser and the condensed vapours were mixed with the liquid leaving the bottom of the reactor, resulting in a crude mixture comprising 0.074% dichloroacetic acid. The final monochloroacetic acid product comprised 0.080% dichloroacetic acid, after distilling off the light and heavy ends.

EXAMPLE 6

A liquid feed of 4,043 kg/h comprising 87.0% monochloroacetic acid, 4.1% dichloroacetic acid, 6.5% acetic acid, 1.9% HCl, and 0.5% water was mixed with 8.91 kg/h hydrogen. The resulting gas-liquid mixture was heated to 171° C. and fed to the top of a vertical column with a diameter of 0.8 m and a length of 16 m. The vertical column was filled with a catalyst comprising 1% of Pd on an activated carbon support (catalyst particles comparable to those described in Example 1 of EP 0557169). The catalyst particles were loaded into the reactor by first filling the reactor with water and (slowly) adding the catalyst. Where necessary, water was allowed to drain via the bottom of the reactor to prevent the reactor from overflowing during its filling with catalyst. The reactor is completely drained after all the required catalyst has been added. The catalyst particles were in the form of extrudates having a diameter of 1.5 mm and an average length over diameter ratio of 1.84. The pressure in the top of the column was maintained at 0.4 MPa. The pressure drop over the vertical column was 33 kPa. The gas flow from the bottom of the reactor was passed over a condenser and the condensed vapours were mixed with the liquid leaving the bottom of the reactor, resulting in a crude mixture comprising 0.068% dichloroacetic acid. The final monochloroacetic acid product comprised 0.074% dichloroacetic acid, after distilling off the light and heavy ends.

The results as shown in Example 5 and Example 6 again show that with an increased acetic acid content in the feed, an even purer product is obtained.

EXAMPLE 7

A liquid feed of 4,043 kg/h comprising 87.0% monochloroacetic acid, 4.1% dichloroacetic acid, 6.5% acetic acid, 1.9% HCl, and 0.5% water was mixed with 8.91 kg/h hydrogen. The resulting gas-liquid mixture was heated to 171° C. and fed to the top of a vertical column with a diameter of 0.6 m and a length of 20 m. The vertical column was filled with a catalyst comprising 1% of Pd on an activated carbon support (catalyst particles comparable to those described in Example 1 of EP 0557169). The catalyst particles were loaded into the reactor by first filling the reactor with water and (slowly) adding the catalyst. Where necessary, water was allowed to drain via the bottom of the reactor to prevent the reactor from overflowing during its filling with catalyst. The reactor is completely drained after all the required catalyst has been added. The catalyst particles were in the form of extrudates having a diameter of 1.5 mm and an average length over diameter ratio of 1.84. The pressure in the top of the column was maintained at 0.4 MPa. The pressure drop over the vertical column was 157 kPa. The gas flow from the bottom of the reactor was passed over a condenser and the condensed vapours were mixed with the liquid leaving the bottom of the reactor, resulting in a crude mixture comprising 0.043% dichloroacetic acid. The final monochloroacetic acid product comprised 0.047% dichloroacetic acid, after distilling off the light and heavy ends.

The results as shown in Example 6 and Example 7 show that with less catalyst (in a column with a smaller diameter), an even purer product is obtained.

EXAMPLE 8

A liquid feed of 4,043 kg/h comprising 87.0% monochloroacetic acid, 4.1% dichloroacetic acid, 6.5% acetic acid, 1.9% HCl, and 0.5% water was mixed with 8.91 kg/h hydrogen. The resulting gas-liquid mixture was heated to 171° C. and fed to the top of a vertical column with a diameter of 0.8 m and a length of 12 m. The vertical column was filled with a catalyst comprising 1% of Pd on an activated carbon support (catalyst particles comparable to those described in Example 1 of EP 0557169). The reactor was filled with catalyst by means of the Densicat® dense loading technique. Other dense loading techniques, including e.g. the Catapac™ dense loading techniques, are also suitable. The catalyst particles were in the form of extrudates having a diameter of 1.5 mm and an average length over diameter ratio of 1.84. The pressure in the top of the column was maintained at 0.4 MPa. The pressure drop over the vertical column was 97 kPa. The gas flow from the bottom of the reactor was passed over a condenser and the condensed vapours were mixed with the liquid leaving the bottom of the reactor, resulting in a crude mixture comprising 0.027% dichloroacetic acid. The final monochloroacetic acid product comprised 0.030% dichloroacetic acid, after distilling off the light and heavy ends.

The difference between Examples 5, 6, 7 and Example 8 is that in Example 8, the catalyst was loaded using a dense loading technique and a high average axial pressure gradient was applied. This results in a pure product.

The invention claimed is:

1. A process comprising subjecting a liquid feed comprising monochloroacetic acid and dichloroacetic acid to a catalytic hydrodechlorination step by contacting it with a source of hydrogen to convert the dichloroacetic acid into monochloroacetic acid in the presence of a solid heterogeneous hydrogenation catalyst comprising one or more metals of Group VIII of the Periodic Table of the Elements deposited on a carrier, wherein said catalytic hydrodechlorination step is carried out in a vertical tubular reactor with a diameter exceeding 0.4 m, with the solid heterogeneous hydrogenation catalyst being situated in a fixed catalyst bed, wherein the liquid feed is fed to the top of said vertical tubular reactor at a superficial mass velocity of between 1 and 10 kg/s per square meter of the horizontal cross-section of the vertical tubular reactor and a rate of between 250 and 3,000 kg/hr per $m^3$ of said catalyst bed, wherein the source of hydrogen is fed to the top or bottom of the vertical tubular reactor at a superficial gas velocity of between 0.025 to 0.25 $Nm^3$/s per square meter of the horizontal cross-section of the vertical tubular reactor, so as to obtain an average axial pressure gradient of at least 2 kPa per meter of said catalyst bed, and wherein the temperature in the top of the vertical tubular reactor is between 100 and 200° C., and wherein the pressure in the top of the vertical tubular reactor is between 0.2 and 1.0 MPa.

2. The process according to claim 1 wherein the liquid feed fed to the top of said vertical tubular reactor comprises at least 5.5% by weight acetic acid.

3. The process according to claim 1 wherein the fixed catalyst bed in which the heterogeneous hydrogenation catalyst is situated has been prepared by loading the vertical tubular reactor with the heterogeneous hydrogenation catalyst using a dense loading technique.

4. The process according to claim 1 wherein the liquid feed is fed to the top of said vertical tubular reactor at a superficial mass velocity of between 2.5 and 6 kg/s per square meter of the horizontal cross-section of the vertical tubular reactor.

5. The process according to claim 1 wherein the heterogeneous hydrogenation catalyst comprises between 0.1 and 3% by weight, based on the total weight of the heterogeneous hydrogenation catalyst, of the one or more metals of Group VIII of the Periodic Table of the Elements.

6. The process according to claim 1 wherein the carrier is selected from the group consisting of activated carbon, silica, alumina, zirconium oxide, and titanium oxide.

7. The process according to claim 6, wherein the carrier is in the form of particles, said particles being in the form of irregularly shaped granules, spheres, rings, trilobes, quadrulobes, or extrudates.

8. The process according to claim 7 wherein the particles are in the form of extrudates, trilobes, or quadrulobes, and wherein said extrudates, trilobes or quadrulobes have a diameter of between 0.8 and 3 mm and a length of between 1 and 10 mm.

9. The process according to claim 1 wherein the heterogeneous hydrogenation catalyst comprises at least one of palladium and platinum.

10. The process according to claim 1 wherein the temperature in the top of the vertical tubular reactor is between 145 and 175° C.

11. The process according to claim 1 wherein the source of hydrogen is fed to the top of the vertical tubular reactor, resulting in a co-current downflow with the liquid feed.

12. The process according to claim 11 wherein the pressure in the top of the vertical tubular reactor is between 0.3 and 0.6 MPa.

13. The process according to claim 1 wherein the source of hydrogen is fed to the bottom of the vertical tubular reactor and the pressure at the bottom of the vertical tubular reactor is between 0.3 and 0.6 MPa.

14. The process according to claim 1 wherein the liquid feed subjected to the catalytic hydrodechlorination step comprises
(i) between 60 and 99.5% by weight of monochloroacetic acid,
(ii) between 0.05 and 20% by weight of dichloroacetic acid,
(iii) between 0 and 30% by weight of acetic acid,
(iv) between 0.1 and 5% by weight of water, and
(v) between 0 and 5% by weight of other components,
up to a total of 100%, based on the total weight of the liquid feed.

15. The process according to claim 3 wherein the liquid feed is fed to the top of said vertical tubular reactor at a superficial mass velocity of between 2.5 and 6 kg/s per square meter of the horizontal cross-section of the vertical tubular reactor.

16. The process according to claim 4 wherein the heterogeneous hydrogenation catalyst comprises between 0.1 and 3% by weight, based on the total weight of the heterogeneous hydrogenation catalyst, of the one or more metals of Group VIII of the Periodic Table of the Elements.

17. The process according to claim 5 wherein the carrier is selected from the group consisting of activated carbon, silica, alumina, zirconium oxide, and titanium oxide.

18. The process according to claim 3 wherein the temperature in the top of the vertical tubular reactor is between 145 and 175° C.

19. The process according to claim 5 wherein the source of hydrogen is fed to the top of the vertical tubular reactor, resulting in a co-current downflow with the liquid feed.

20. The process according to claim 9 wherein the source of hydrogen is fed to the bottom of the vertical tubular reactor and the pressure at the bottom of the vertical tubular reactor is between 0.3 and 0.6 MPa.

* * * * *